(12) United States Patent
Araki et al.

(10) Patent No.: US 8,417,548 B2
(45) Date of Patent: Apr. 9, 2013

(54) MEDICAL SERVICE SUPPORT APPARATUS

(75) Inventors: Hiroyuki Araki, Sagamihara (JP);
Takashi Hosaka, Mitaka (JP);
Masakazu Omura, Yokohama (JP);
Yusuke Kato, Chofu (JP); Emiko Ouchi, Chofu (JP); Ryoichi Hosoya, Orefield, PA (US)

(73) Assignee: Olympus Medical Systems Corp., Tokyo (JP)

( * ) Notice: Subject to any disclaimer, the term of this patent is extended or adjusted under 35 U.S.C. 154(b) by 168 days.

(21) Appl. No.: 13/091,833

(22) Filed: Apr. 21, 2011

(65) Prior Publication Data

US 2011/0288885 A1    Nov. 24, 2011

Related U.S. Application Data

(63) Continuation of application No. PCT/JP2010/006229, filed on Oct. 20, 2010.

(30) Foreign Application Priority Data

Oct. 21, 2009   (JP) ................................ 2009-242813

(51) Int. Cl.
*G06Q 50/00*    (2006.01)
(52) U.S. Cl. .......................................................... 705/3
(58) Field of Classification Search ................... 705/2, 3
See application file for complete search history.

(56) References Cited

U.S. PATENT DOCUMENTS

| | | | |
|---|---|---|---|
| 7,577,573 B2 * | 8/2009 | Janas et al. | 705/2 |
| 7,769,600 B2 * | 8/2010 | Iliff | 705/2 |
| 7,822,622 B2 * | 10/2010 | Kaindl et al. | 705/2 |
| 7,831,444 B2 * | 11/2010 | Brown et al. | 705/2 |
| 2004/0078232 A1 * | 4/2004 | Troiani | 705/2 |

FOREIGN PATENT DOCUMENTS

| | | |
|---|---|---|
| JP | 2005-004260 | 1/2005 |
| JP | 2005-301600 A | 10/2005 |
| JP | 2006-116034 | 5/2006 |
| JP | 2006-277656 A | 10/2006 |
| JP | 2008-204378 A | 9/2008 |

OTHER PUBLICATIONS

Takahiro, Fujii, et al. Japanese Polyp Study, National Polyp Study, Apr. 25, 2002, pp. 439 to 445.

(Continued)

*Primary Examiner* — Gerald J. O'Connor
*Assistant Examiner* — Jonathan K Ng
(74) *Attorney, Agent, or Firm* — Scully, Scott, Murphy & Presser, P.C.

(57) ABSTRACT

A recording unit holds a plurality of examination data including the examination date of a performed examination. A search unit extracts examination data matching a set condition, of the plurality of examination data held in the recording unit. An output unit outputs a search result by the search unit. A first narrowing unit extracts examination data in which the examination date is included within a designated first period. A reference data determination unit classifies the examination data extracted by the first narrowing unit by an examinee and determines, for every examinee, one piece of the examination data to be a reference in accordance with a predetermined rule. A second narrowing unit sets, for every examinee, a second period designated in at least one of the past direction and the future direction starting from a reference date that is the examination date of the examination data determined by the reference data determination unit and extracts examination data in which the examination date is included within the second period.

2 Claims, 13 Drawing Sheets

OTHER PUBLICATIONS

International Search Report PCT/JP2010/006229 dated Dec. 14, 2010.

International Preliminary Report on Patentability and Written Opinion of the International Searching Authority dated May 15, 2012 from corresponding Japanese Patent Application PCT/JP2010/006229, together with English language translation.

Nakashima Yoshiaki, et al., "Relation between interval of US examination and progress of hepatocellular carcinoma at detection", Japanese Journal of Radiological. Technology, Aug. 1, 1997, vol. 50, No. 8 (consecutive number of vols. 286), p. 1227, together with English language translation.

Suga Machi, et al., "Consideration regarding Proper Interval for Conducting Medical Checkup", Journal of Health and Welfare Statistics, Japan, Health Labour and Welfare Statistics Association, May 15, 2007, vol. 54, No. 5 (consecutive number of vols. 844), p. 31-36, together with English language translation.

Japanese Office Action dated Jul. 12, 2011 from corresponding Japanese Patent Application No. 2011-517544 together with partial English language translation.

* cited by examiner

FIG.2

| EXAMINA-TION ID | PATIENT INFORMATION ||||  EXAMINA-TION DATE | EXAMINATION TYPE | FINDING | DIAGNOSIS |
| --- | --- | --- | --- | --- | --- | --- | --- | --- |
| 21 | PATIENT ID | NAME | AGE | SEX | 23 | 24 | 25 | 26 |
|  | 22 ||||  |  |  |  |
| 0001 | 0001 | XX XX | 50 YEARS OLD | MAN | 2005 10 5 | UPPER ENDOSCOPY EXAMINATION | MULTIPLE POLYPS IN GASTRIC BODY | GASTRIC POLYP GASTRIC INFLAMMATION |
| 0002 | 0002 | YY YY | 45 YEARS OLD | WOMAN | 2005 10 6 | LOWER ENDOSCOPY EXAMINATION | NO ABNORMALITY |  |
| ...... |  |  |  |  |  |  |  |  |

```
┌─────────────────────────────────────────────────────────────┐
│                    CONDITION SEARCH                          │
│                           611a              611b             │
│ ■SEARCH PERIOD  [JANUARY 1, 2005]  ~  [DECEMBER 31, 2005]    │
│                                                              │
│ ■SEARCH CONDITION                             612            │
│                 ┌──────────────────────────────────┐         │
│                 │SEARCH FORMULA                    │         │
│                 │ EXAMINATION TYPE = UPPER ENDOSCOPE│        │
│                 │                    EXAMINATION   │         │
│                 │                                  │         │
│                 │                                  │         │
│                 └──────────────────────────────────┘         │
│                                               613            │
│ ■CASE-NUMBER   .NUMBER OF EXAMINATIONS.NUMBER OF PATIENTS    │
│    DISPLAY         2500 CASES            2400 CASES          │
│   614          615           616              617            │
│ ┌──────┐   ┌─────────┐   ┌───────┐   ┌───────────────┐       │
│ │SEARCH│   │CONDITION│   │ LIST  │   │ TO TEMPORAL   │       │
│ │      │   │  CLEAR  │   │DISPLAY│   │ AXIS SEARCH   │       │
│ └──────┘   └─────────┘   └───────┘   └───────────────┘       │
└─────────────────────────────────────────────────────────────┘
                              61
```

FIG.12

```
┌─────────────────────────────────────────────────────────────┐
│                   TEMPORAL AXIS SEARCH                       │
│                           621a         621b                  │
│ ■TEMPORAL SEARCH    [THREE YEARS]    [FUTURE]                │
│   PERIOD LENGTH                                              │
│ ■SEARCH CONDITION                              622           │
│                 ┌──────────────────────────────────┐         │
│                 │SEARCH FORMULA                    │         │
│                 │ EXAMINATION TYPE = UPPER ENDOSCOPE│        │
│                 │                    EXAMINATION   │         │
│                 │ & WORD = POLYP                   │         │
│                 │                                  │         │
│                 └──────────────────────────────────┘         │
│                                                623           │
│ ■CASE-NUMBER   .NUMBER OF EXAMINATIONS.NUMBER OF PATIENTS    │
│    DISPLAY          TEN CASES             TEN CASES          │
│   624          625           626              627            │
│ ┌──────┐   ┌─────────┐   ┌───────┐   ┌──────────┐            │
│ │SEARCH│   │CONDITION│   │ LIST  │   │  RETURN  │            │
│ │      │   │  CLEAR  │   │DISPLAY│   │          │            │
│ └──────┘   └─────────┘   └───────┘   └──────────┘            │
└─────────────────────────────────────────────────────────────┘
                              62
```

MEDICAL SERVICE SUPPORT APPARATUS

BACKGROUND OF THE INVENTION

1. Field of the Invention

The present invention relates to a medical service support apparatus for managing examination data.

2. Description of the Related Art

In recent years, medical service support systems for performing medical services more efficiently have been widely used. For example, an endoscope service support system for endoscopic departments has been put in practical use. In the system, medical information indicating "when", "where", "by who", "to whom", "what", and "why" a medical service has been performed, can be accurately stored and managed, the medical information being acquired from the reception to the examination, diagnosis, and conference at an endoscopic department. Doctors and managers at a hospital can utilize the data recorded in the system for treatments, researches, and administrative improvement, etc.

[Patent Documents]

[Patent Document 1] Japanese Patent Application Publication No. 2005-4260

[Patent Document 2] Japanese Patent Application Publication No. 2006-116034

Early detection is extremely important for the treatments of the overall diseases including cancer, arteriosclerosis, etc. Although it is needed to frequently perform examinations for early detection, the financial situations of developed countries including Japan have been tight, and there are strong pressure to cut the medical expenses. Accordingly, it is required to perform examinations at optimal intervals, not too short and not too long.

SUMMARY OF THE INVENTION

A medical service support apparatus according to an embodiment of the present invention comprises: a recording unit configured to hold a plurality of examination data including the examination date of a performed examination; a search unit configured to extract examination data matching a set condition, of the plurality of examination data held in the recording unit; and an output unit configured to output a search result by the search unit. The search unit includes: a first narrowing unit configured to extract examination data in which the examination date is included within a designated first period; a reference data determination unit configured to classify the examination data extracted by the first narrowing unit by an examinee and to determine, for every examinee, one piece of the examination data to be a reference in accordance with a predetermined rule; and a second narrowing unit configured to set, for every examinee, a second period designated in at least one of the past direction and the future direction starting from a reference date that is the examination date of the examination data determined by the reference data determination unit and to extract examination data in which the examination date is included within the second period.

It is noted that any combination of the aforementioned components or any manifestation of the present invention exchanged between methods, devices, systems, recording media, computer programs, and so forth, is effective as an embodiment of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 2 is a view illustrating an example of a format of examination data;

FIG. 11 is a view illustrating an example of a condition search screen displayed on the display of an output unit;

FIG. 12 is a view illustrating an example of a temporal axis search screen displayed on the display of the output unit;

DETAILED DESCRIPTION OF THE INVENTION

The invention will now be described by reference to the preferred embodiments. This does not intend to limit the scope of the present invention, but to exemplify the invention.

Figure 1:
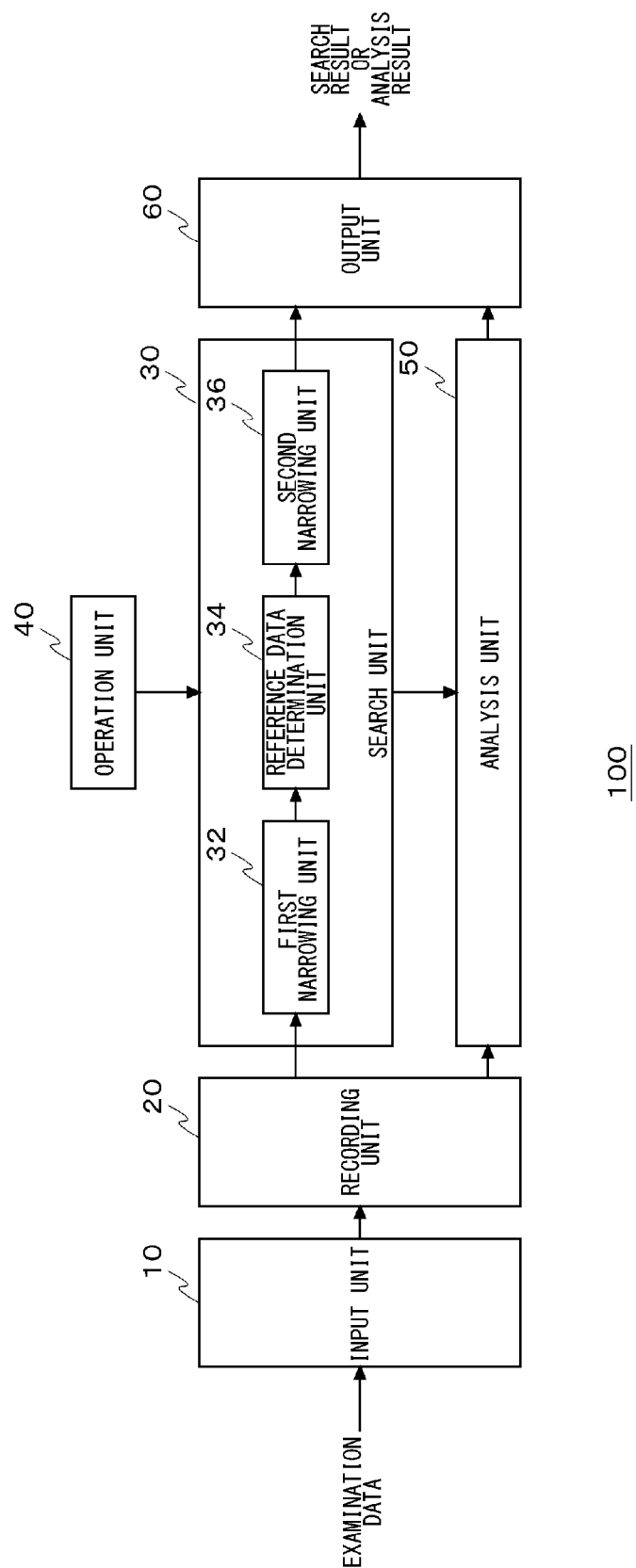
FIG. 1 illustrates the configuration of a medical service support apparatus according to an embodiment of the present invention.

FIG. 1 is a view illustrating the configuration of a medical service support apparatus 100 according to an embodiment of the present invention. The medical service support apparatus 100 can be structured by at least one server or PC. The medical service support apparatus 100 comprises an input unit 10, a recording unit 20, a search unit 30, an operation unit 40, an analysis unit 50, and an output unit 60. The search unit 30 includes a first narrowing unit 32, a reference data determination unit 34, and a second narrowing unit 36.

These elements are implemented by hardware including an arbitrary processor, a memory, and another LSI, and by software including a program loaded into the memory or the like. Herein, the functional blocks realized by the cooperation thereof are illustrated. Accordingly, it should be understood by a person skilled in the art that these functions can be realized in various forms by hardware only, software only, or combination thereof.

The input unit 10 records examination data into the recording unit 20 by acquiring the examination data from outside. For example, the input unit 10 records examination data into the recording unit 20 by acquiring the examination data from a non-illustrated endoscope system via a network. The examination data is one in which an examination performed on an examinee has been recorded. The examination data is generated for every examination and includes at least items of patient information, examination date, examination type, findings, and diagnosis. A format example thereof will be described later.

The recording unit 20 holds a plurality of examination data recorded by the input unit 10.

Of the plurality of examination data held in the recording unit 20, the search unit 30 extracts the examination data matching a set condition. The detailed configuration of the search unit 30 will be described later.

The operation unit 40 receives a direction from a user. In the present embodiment, the operation unit 40 mainly receives the aforementioned set condition and sets it in the search unit 30.

The analysis unit 50 performs various analyses by using the plurality of examination data held in the recording unit 20. The analysis functions by the analysis unit 50 can be utilized in the service analysis for administrative improvement. More specifically, an operating rate of every endoscope model, an examination operating rate per unit time, medical service fee per unit time, operating time of each examination, and performance transition of each day of the week and each examination type, etc., can be calculated. The analysis functions by the analysis unit 50 can also be utilized in supporting the service and research of doctors.

The output unit 60 outputs an analysis result by the search unit 30 or the analysis unit 50. For example, a search result or analysis result may be displayed on a display, printed as a report, or file-outputted.

Hereinafter, the search unit 30 will be described more specifically. Of the plurality of examination data recorded in the recording unit 20, the first narrowing unit 32 extracts examination data in which the examination date is included within a designated first period. The first period is set from the operation unit 40 in accordance with an operation of a user.

Alternatively, the first narrowing unit 32 may extract examination data in which the examination date is included within the first period and in which another condition is satisfied. As the another condition, the fact that an examinee has been diagnosed as being affected by a specific disease can be cited. Multiple conditions may be set as the another condition. The conditions with regard to, for example, age, sex, anamnesis, and family history, may be added. In this case, the first narrowing unit 32 extracts examination data in which the examination date is included within the first period and in which multiple another conditions are all satisfied.

The reference data determination unit 34 classifies the examination data extracted by the first narrowing unit 32 by an examinee and determines, for every examinee, one piece of the examination data to be a reference in accordance with a predetermined rule. For example, of the examination data extracted by the first narrowing unit 32, the reference data determination unit 34 determines, for every examinee, examination data in which the examination date is oldest or latest as the examination data to be a reference.

The second narrowing unit 36 sets, for every examinee, a second period designated in at least one of the past direction and the future direction starting from a reference date that is the examination date of the examination data determined by the reference data determination unit 34 and extracts examination data in which the examination date is included within the second period. The second period is also set from the operation unit 40 in accordance with an operation of a user.

Alternatively, the second narrowing unit 36 may also extract, for every examinee, examination data in which the examination date is included within the second period and in which another condition is satisfied. As the another condition, the fact that an examinee has been diagnosed as being affected by a specific disease can be cited. Multiple conditions may be set as the another condition. In this case, the second narrowing unit 36 extracts, for every examinee, examination data in which the examination date is included within the second period and in which multiple another conditions are satisfied.

FIG. 2 is a view illustrating an example of a format of examination data. The examination data held in the recording unit 20 includes items of an examination ID 21, patient information 22, examination date 23, examination type 24, findings 25, and diagnosis 26. The patient information 22 includes sub-items of a patient ID, name, age, and sex. Each of the items included in the format of examination data is cited as an example, and items of an examination doctor, used equipment, and used medicine, etc., may be included. Further, in an example of endoscopic examination, items of an examined area and presence/absence of biopsy, etc., may be additionally included.

Figure 3:
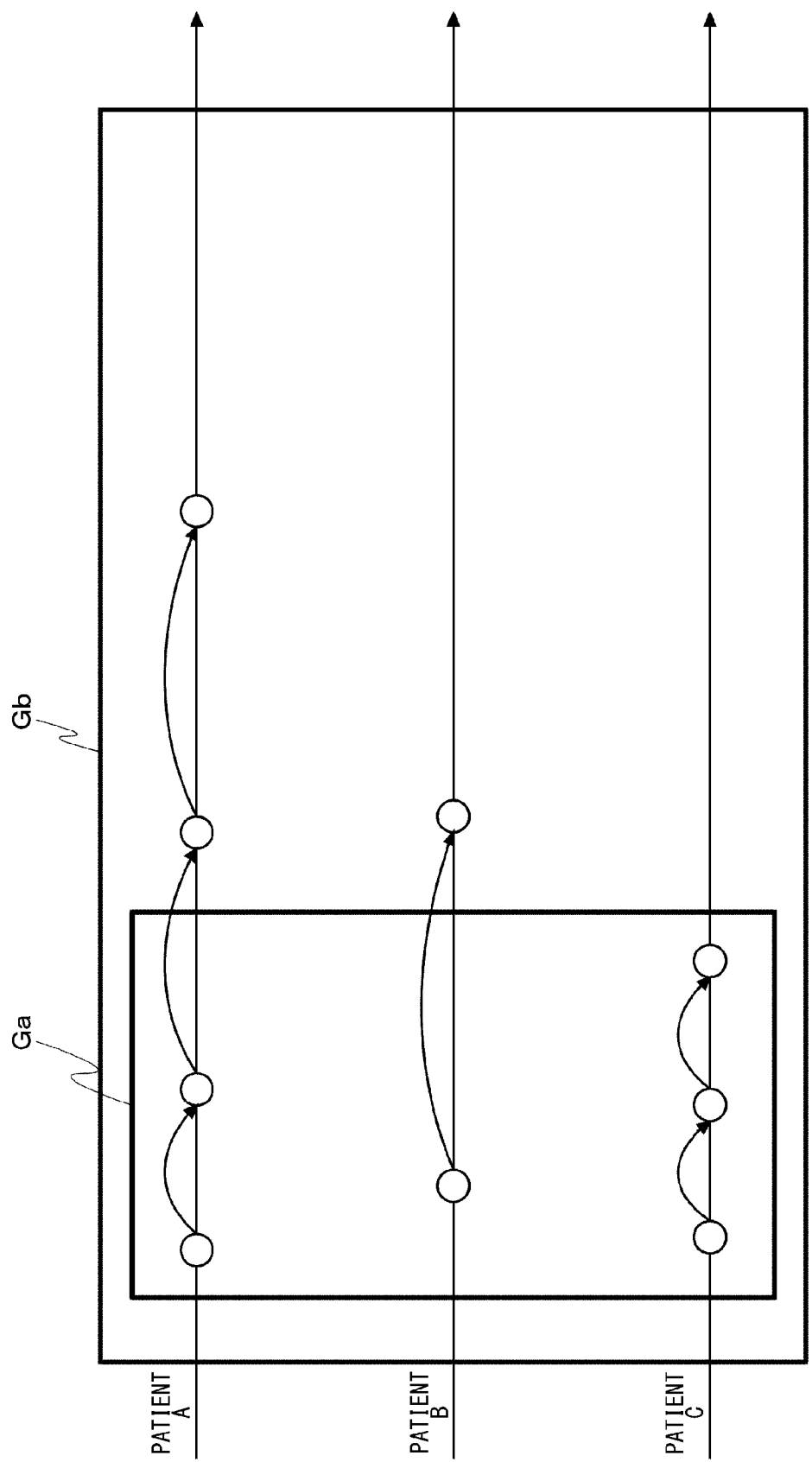
FIG. 3 is a view for explaining the basic concept of temporal axis search executable by a search unit.

FIG. 3 is a view for explaining the basic concept of temporal axis search executable by search unit 30. Of the many examination data held in the recording unit 20, the first narrowing unit 32 first extracts the examination data included in a group A (Ga), each of which is to be reference data. Examinees who have undergone the examinations included in the group A (Ga) (hereinafter, referred to as patients including an examinee whose abnormality has not been detected) are listed by this extraction.

Of the examination data of the patients listed by the first narrowing unit 32, the second narrowing unit 36 subsequently extracts the examination data included in a group B (Gb). Thereby, time-series examination data of the listed patients, in which the aforementioned reference data are included, are extracted. The analysis unit 50 can specify, based on the time-series examination data of every patient, each examination interval from the examination dates of two adjacent examination data.

Figure 4:
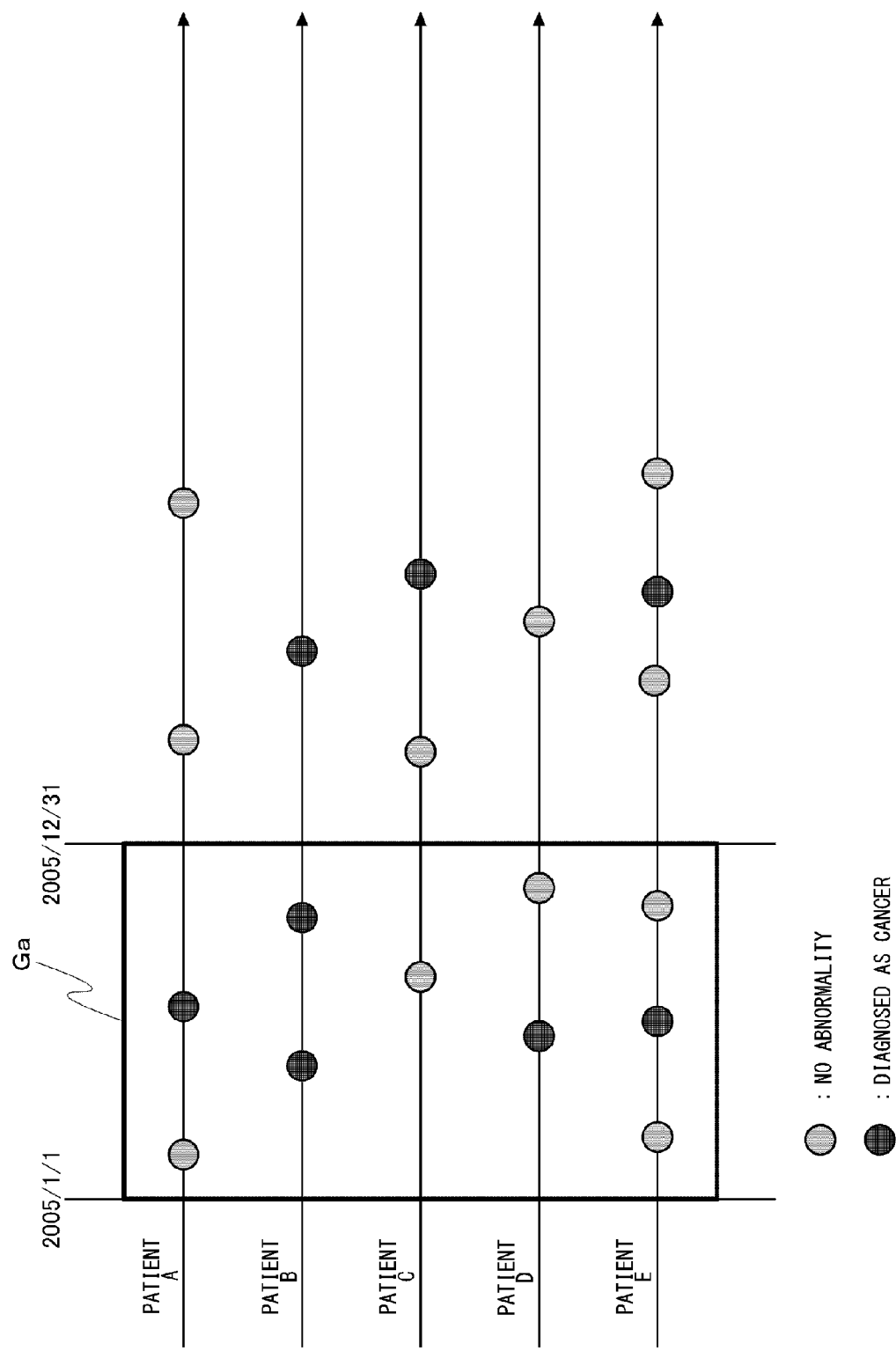
FIG. 4 is a view for explaining extraction of patients by the temporal axis search.

FIG. 4 is view for explaining extraction of patients by the temporal axis search. In FIG. 4, examination data in which the examination date is included within a period of Jan. 1, 2005 to Dec. 31, 2005, are extracted. The patients who have undergone the examination within the period are extracted by this extraction. Five patients A to E are extracted in FIG. 4. Further, a type of examination may be designated. That is, the examination data with respect to a specific type of examination performed within the period of Jan. 1, 2005 to Dec. 31, 2005, may be extracted.

Figure 5:
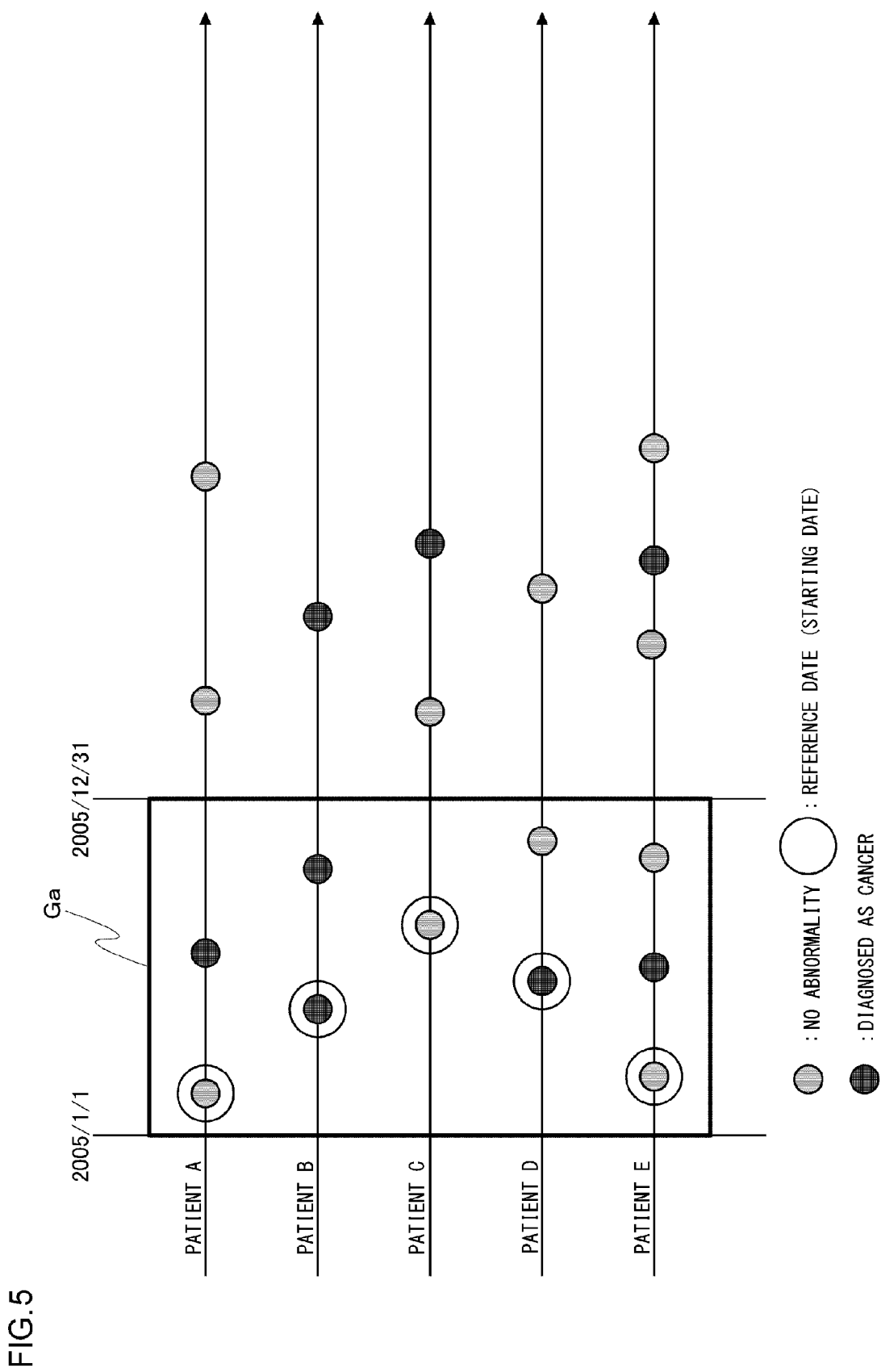
FIG. 5 is a view for explaining a first method of determining the reference date of each patient.

FIG. 5 is a view for explaining a first method of determining the reference date of each patient. In the first determination method, of the examination data included in the group A (Ga), the examination date of examination data in which the examination date is oldest is set to be a reference date (i.e., the starting date of the time-series) for every patient. In FIG. 5, of the examinations that the patients A to E have undergone during a period of Jan. 1, 2005 to Dec. 31, 2005, the oldest examination date is set to be a reference date. Alternatively, of the examination data included in the group A (Ga), the examination date of examination data in which the examination date is latest may be set to be a reference date for every patient.

When time-series examination data are extracted in the past direction, it is better to select the latter way. In the first determination method, presence/absence of abnormality in each examination data is not in question.

Figure 6:
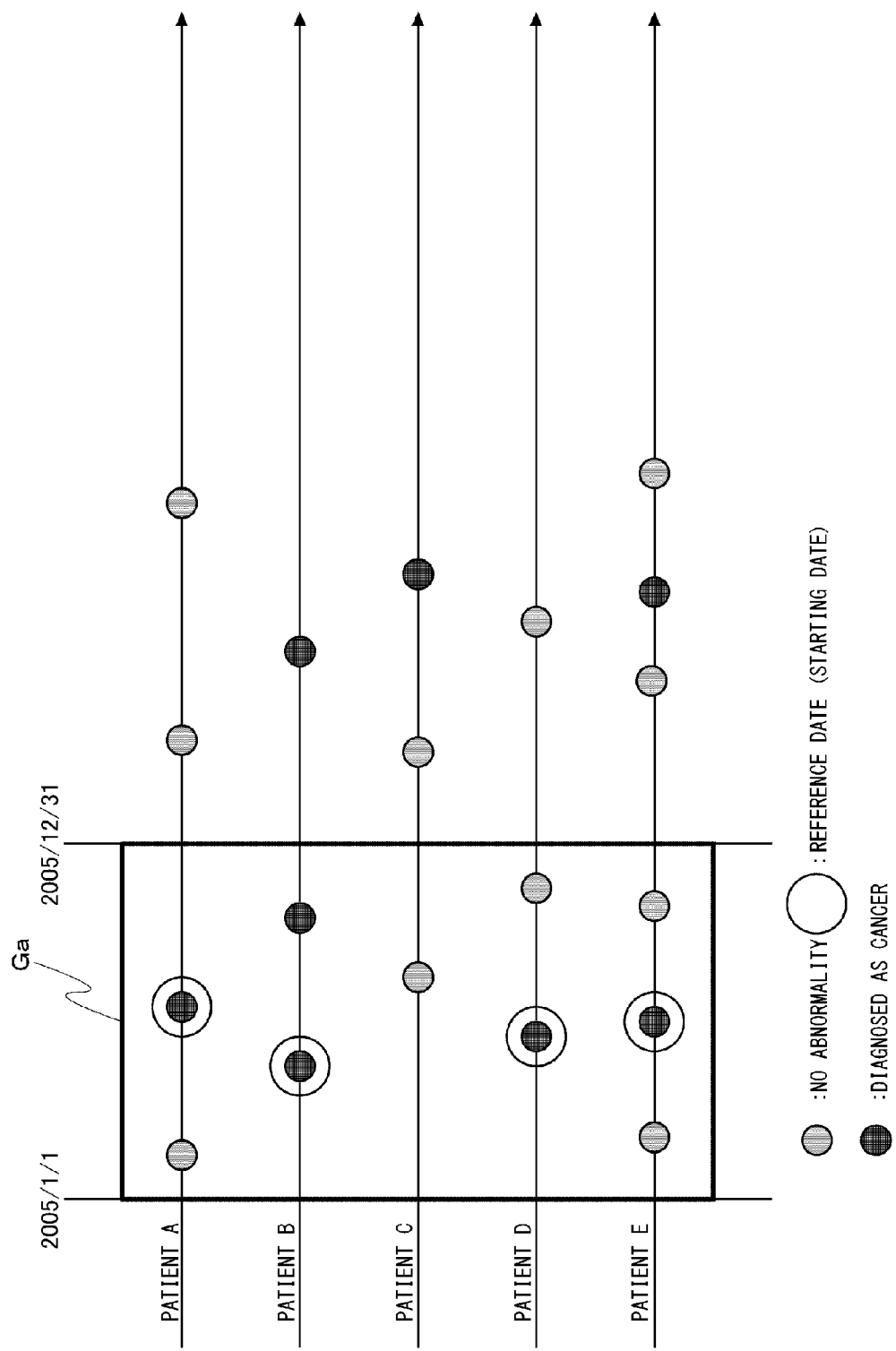
FIG. 6 is a view for explaining a second method of determining the reference date of each patient.

FIG. 6 is a view for explaining a second method of determining the reference date of each patient. In the second determination method, of the examination data included in the group A (Ga) and in which an examinee has been diagnosed as being affected by a specific disease (herein, cancer), the examination date of examination data in which the examination date is oldest is set to be a reference date for every patient. In FIG. 6, because a patient C has no examination data in which the patient C has been diagnosed as being affected by a specific disease during a period of Jan. 1, 2005 to Dec. 31, 2005, the patient C is excluded from the targets of the temporal axis search. Because each of patients A and C has no abnormality in the first examination during the period and has been diagnosed as being affected by cancer in the second examination, the examination date of the second examination is set to be a reference date.

Figure 7:
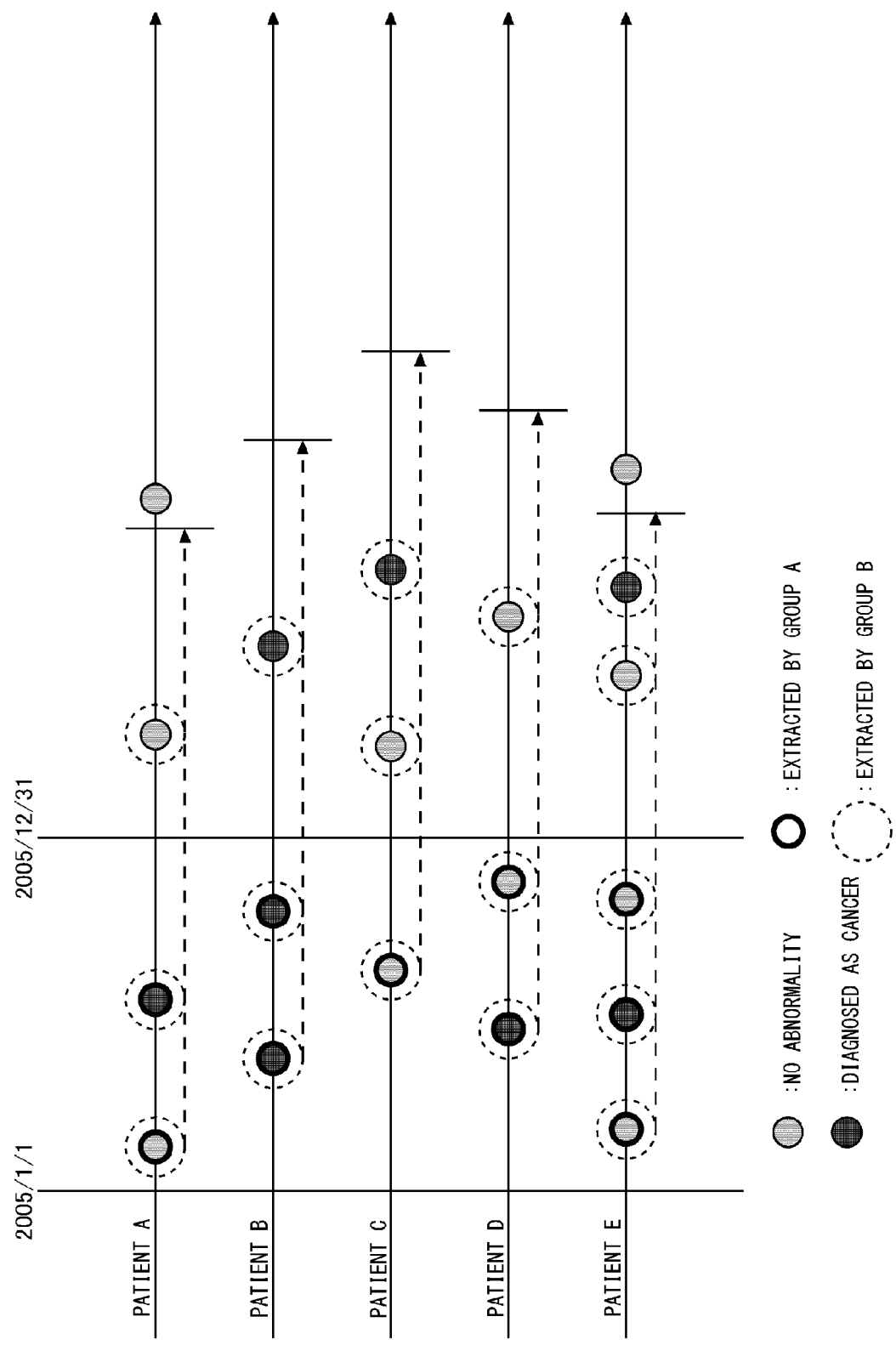
FIG. 7 is a view for explaining (first) extraction of the time-series examination data of extracted patients.

FIG. 7 is a view for explaining (first) extraction of the time-series examination data of extracted patients. FIG. 7 illustrates an example in which it is assumed that a reference date is set by the aforementioned first determination method. In FIG. 7, the examination data of the examinations performed during a predetermined period (e.g., during three years) in the future direction starting from the reference date of an extracted patient are extracted. The dashed arrow lines illustrate extraction periods for every patient, respectively. Examination data out of the extraction period is not extracted. In FIG. 7, the latest examination data of each of patients A and C is not extracted. In FIG. 7, presence/absence of abnormality in each examination data is not in question.

Figure 8:
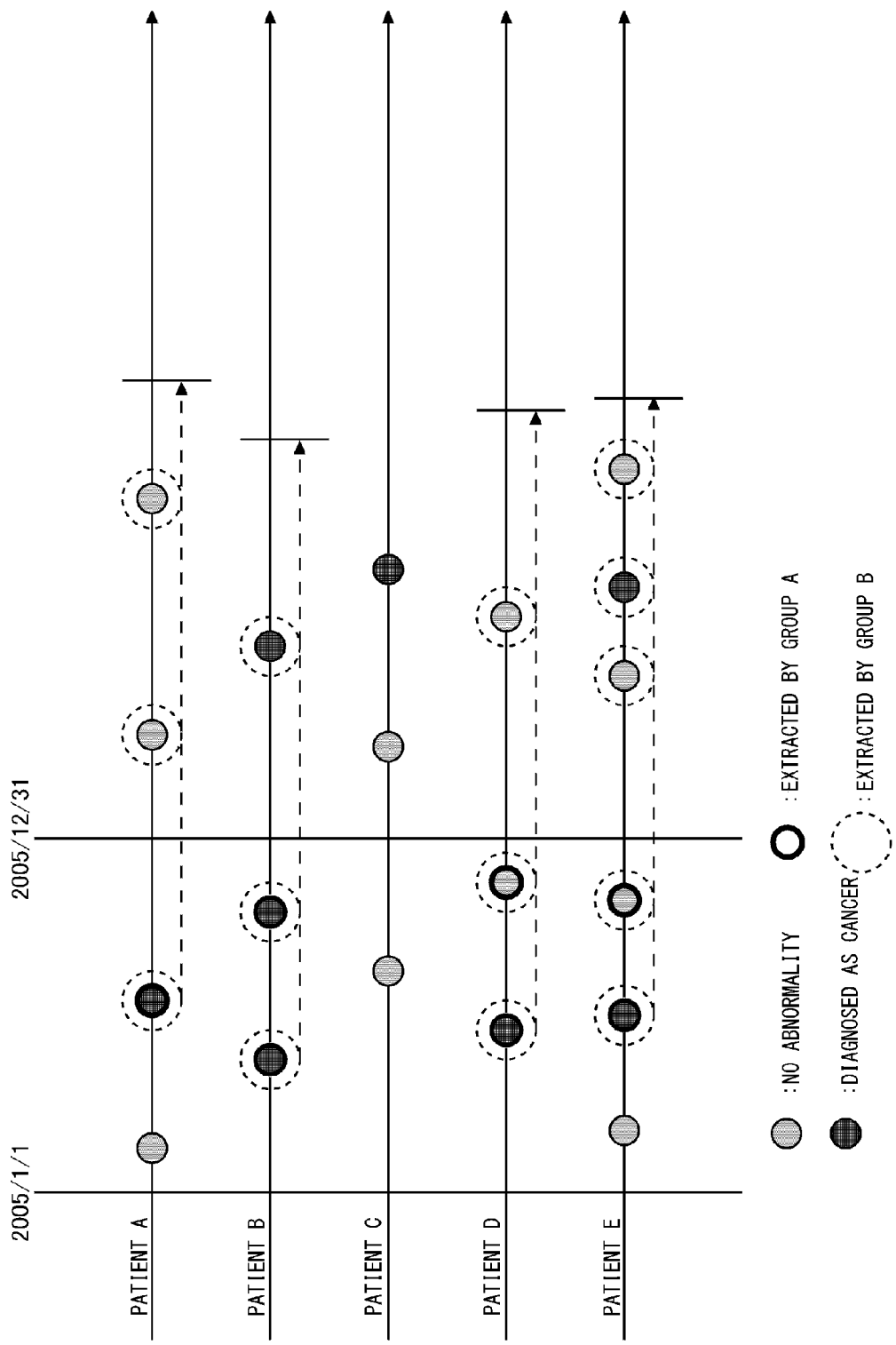
FIG. 8 is a view for explaining (second) extraction of the time-series examination data of the extracted patients.

FIG. 8 is a view for explaining (second) extraction of the time-series examination data of the extracted patients. FIG. 8 illustrates an example in which it is assumed that a reference date is set by the aforementioned second determination method. In FIG. 8, the examination data of the examinations performed during a predetermined period (e.g., during three years) in the future direction starting from the reference date of the extracted patients are extracted. Because it is assumed that a reference date is set by the aforementioned second determination in FIG. 8, the patient C is excluded from the target, as stated above. Because the reference dates of the patients A and C are close to the present time in comparison with those in FIG. 7, the latest examination data of the patients A and C are also extracted in FIG. 8. Also, in FIG. 8, presence/absence of abnormality in each examination data is not in question.

Figure 9:
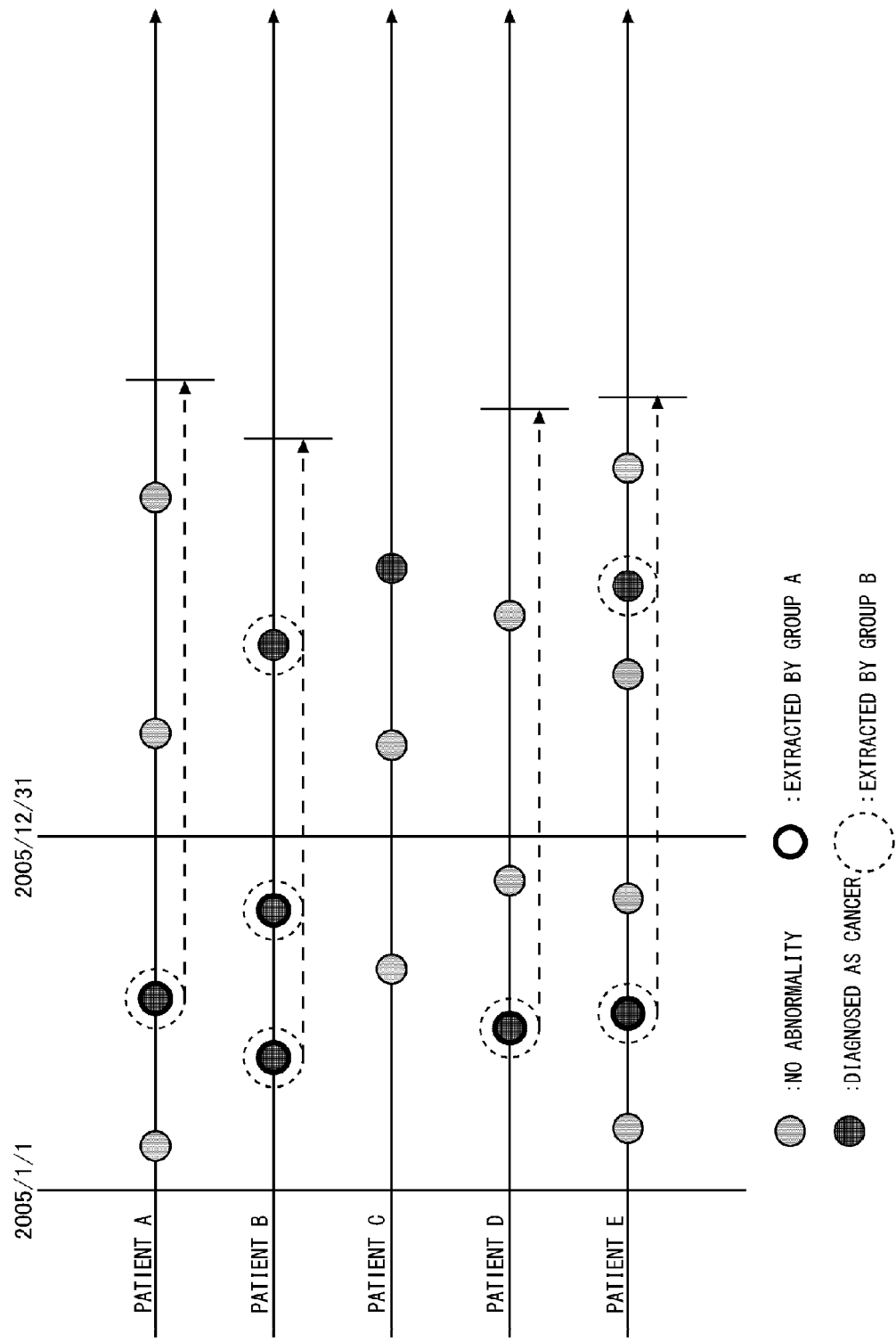
FIG. 9 is a view for explaining (third) extraction of the time-series examination data of the extracted patients.

FIG. 9 is a view for explaining (third) extraction of the time-series examination data of the extracted patients. FIG. 9 also illustrates an example in which it is assumed that a reference date is set by the aforementioned second determination method. In FIG. 9, the examination data of the examinations performed during a predetermined period (e.g., during three years) in the future direction starting from the reference date of an extracted patient and in each of which a patient has been diagnosed as being affected by cancer are extracted.

Figure 10:
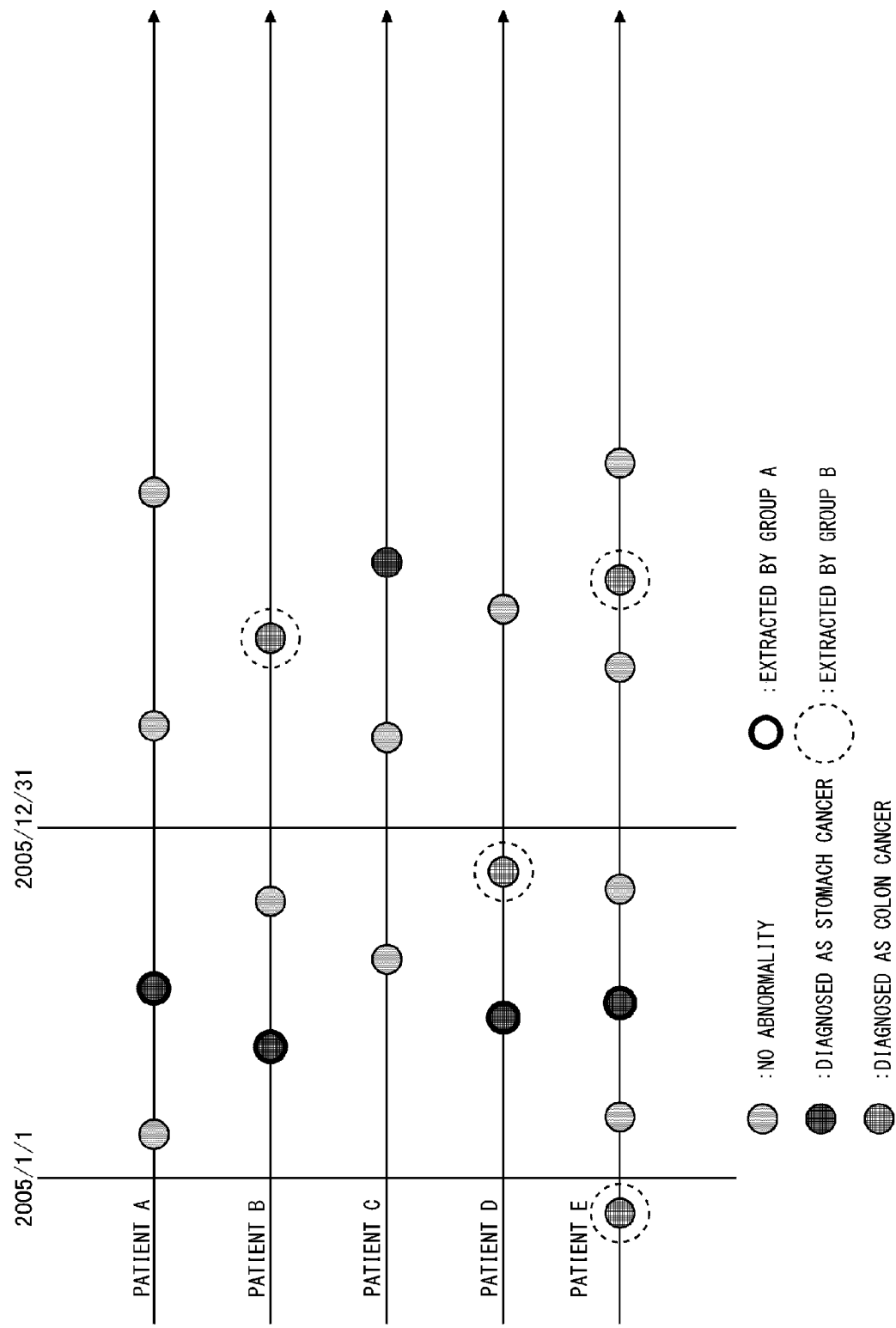
FIG. 10 is a view for explaining (fourth) extraction of the time-series examination data of the extracted patients.

FIG. 10 is a view for explaining (fourth) extraction of the time-series examination data of the extracted patients. In the example, patients each having the examination data included in the group A (Ga) and in which each patient has been diagnosed as being affected by a first disease (stomach cancer in FIG. 10) are extracted. In FIG. 10, the patients A, B, D, and E are extracted. Of the examination data of the extracted patients, the examination data of examinations in each of which a patient has been diagnosed as being affected by a second disease (colon cancer in FIG. 10) are subsequently extracted.

FIG. 11 is a view illustrating an example of a condition search screen 61 displayed on the display of the output unit 60. The condition search screen 61 is one for extracting a patient to be a target of the temporal axis search. On the condition search screen 61, the starting date of a search period is inputted in a first search period field 611*a* and the end data thereof is inputted in a second search period field 611*b*. A search formula is inputted in a search condition field 612.

The number of the examination data (specifically, the numbers of examinations and patients) that are included in the search period and that satisfy the search condition is displayed in an case-number output field 613. The condition search screen 61 includes a search key 614, a condition clear key 615, a list display key 616, and a temporal axis search key 617. When the temporal axis search key 617 is selected and performed of the keys, the condition search screen makes a transition to a temporal axis search screen.

FIG. 12 is a view illustrating an example of the temporal axis search screen 62 displayed on the display of the output unit 60. The temporal axis search screen 62 is one for extracting the time-series examination data of the patients extracted by the aforementioned condition search. On the temporal axis search screen 62, a search period from the reference date of each patient is inputted in a first temporal axis search length field 621*a*, and it is inputted in a second temporal axis search length field 621*b* whether the search period is to be set in the past direction or the future direction. A search formula is inputted in a search condition field 622. Herein, a word search formula with an AND-condition is added. The search formula in FIG. 12 is used for extracting examination data whose examination type is an upper endoscopy examination and that includes a word of "polyp" in the finding and diagnosis.

The number of examination data (specifically, the numbers of examinations and patients), which are included in the aforementioned search period from the reference date of each patient and satisfy the aforementioned search condition, is displayed in a number-of-cases output filed 623. A search key 624, a condition clear key 625, a list display key 626, and a return key 627 are included on the temporal axis search screen 62.

Subsequently, processing of calculating a recommended examination interval by the analysis unit 50 will be described. The analysis unit 50 calculates, for every patient who has been affected by a specific disease, the days that is a difference between the examination date of examination data in which no abnormality has been detected and that of the subsequent examination data in which the patient has been diagnosed as being affected by the disease, by using the plurality of examination data held in the recording unit 20, and performs statistical processing on the days. Thereby, a recommended examination interval of the disease is determined. Hereinafter, more specific description will be made.

Figure 13:
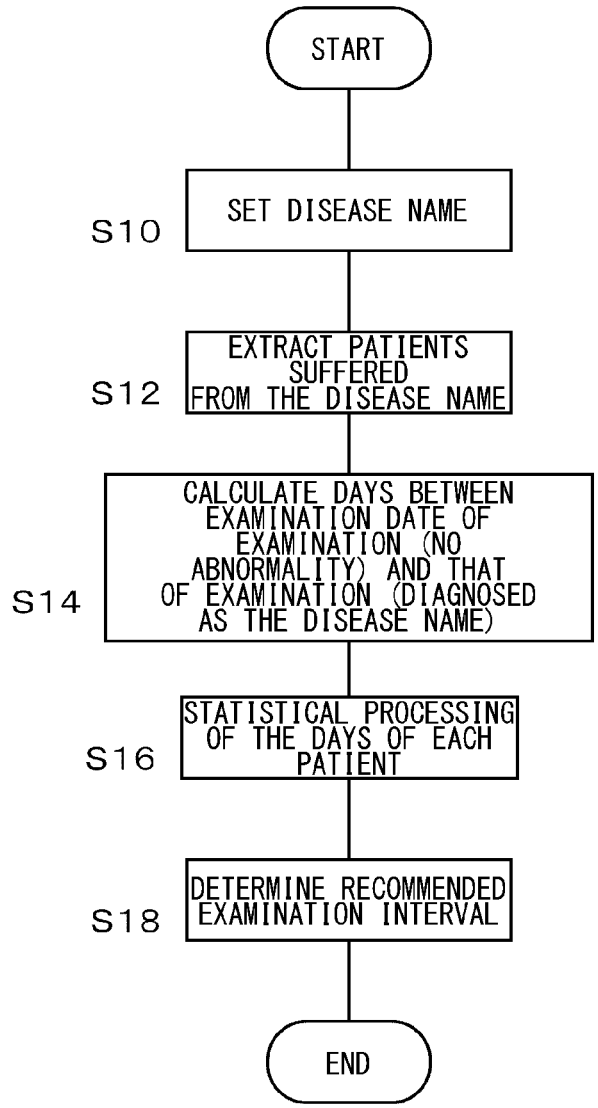
FIG. 13 is a flowchart illustrating an example of processing of calculating a recommended examination interval by an analysis unit.

FIG. 13 is a flowchart illustrating an example of the processing of calculating a recommended examination interval by the analysis unit 50. A user first sets a disease name in the search unit 30 by inputting it in the operation unit 40 (S10). The search unit 30 extracts the patients diagnosed as being affected by the disease name (S12). The analysis unit 50 specifies, for every extracted patient, the examination date of examination in which the patient has been diagnosed as being affected by the disease name and that of the previous examination in which no abnormality has been detected, the latter examination date being closest to the former examination date that is a reference date in the past direction starting from the reference date, and calculates the days between both the examination dates (S14).

The analysis unit 50 performs statistical processing on the days of each patient (S16). For example, a frequency distribution table may be created by classifying the days by multiple ranks. The analysis unit 50 determines, based on a result of the statistical processing, a recommended examination interval of a disease related to the disease name (S18). When the frequency distribution table is created, a recommended examination interval may be determined as follows: multiple ranks in which a specific ratio (e.g., 99 percent) of the parent population is included, counting from the longest days, are specified; and the days representing the smallest rank of the multiple ranks is made to be a recommended examination interval. Alternatively, after the mean (m) and the standard deviation (σ) of the days of each patient are calculated, the days corresponding to (m−3σ) may be made to be a recommended examination interval.

Figure 14:
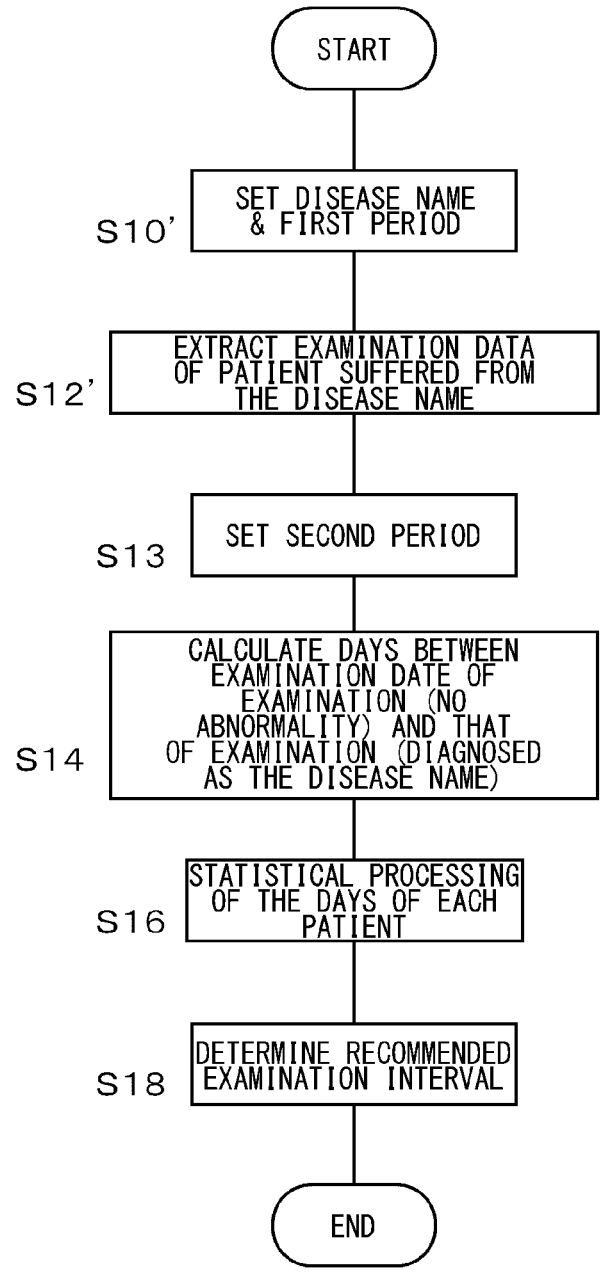
FIG. 14 is a flowchart illustrating another example of the processing of calculating the recommended examination interval by the analysis unit.

Subsequently, an example in which a recommended examination interval is calculated by using the aforementioned temporal axis search function will be described. FIG. 14 is a flowchart illustrating another example of the processing of calculating a recommended examination interval by the analysis unit 50. A user sets a disease name and the aforementioned first period in the search unit 30 by inputting them in the operation unit 40 (S10'). The first narrowing unit 32 extracts examination data in which the examination date is included within the first period and in which a patient has been diagnosed as being affected by the disease name (S12'). Of the examination data extracted by the first narrowing unit 32, the reference data determination unit 34 determines, for every patient, examination data in which the examination date is latest as the examination data to be a reference.

A user sets the aforementioned second period in the search unit 30 by inputting it in the operation unit 40 (S13). Alternatively, it is also possible to set the second period to be limitless. With the examination date of the examination data determined by the reference data determination unit 34 being a reference date, the second narrowing unit 36 extracts, for every patient, examination data in which the examination date is included within the second period in the past direction starting from the reference date and in which no abnormality has been detected, and provides the examination data to the analysis unit 50.

The analysis unit 50 specifies, for every patient, the examination date of examination in which a patient has been diagnosed as being affected by the disease name and that of the previous examination in which no abnormality has been detected, the latter examination date being closest to the former examination date that is a reference date in the past direction starting from the reference date, and calculates the days between both the examination dates (S14). The analysis unit 50 performs statistical processing on the days of each patient (S16), and determines, based on a result of the statistical processing, a recommended examination interval of a disease related to the disease name (S18).

The recommended examination interval may be used for the researches by doctors, or be used in determining when the next examination is performed. For example, when a report on the performed examination is created, a doctor may confirm when the next examination is performed by making the analysis unit 50 calculate the recommended examination interval. The doctor may adopt the examination time as it is, or hold the examination time as reference data to determine when the next examination is performed, also taking into consideration the experiences of the doctor.

According to the present embodiment, the progression of a patient who has been affected by a disease during a period can be easily searched by the aforementioned temporal axis search, as described above. In the medical field, medical devices, medicines, and operative methods progress year by year, and accordingly a method of treatment is sometimes changed drastically at some point. In the case, the data are qualitatively different before and after the change. According to the embodiment, a search in view of when the method of treatment has been changed can be easily performed.

A significant difference in the recurrence interval and the metastasis interval of a cancer, etc., is sometimes created before and after a change in a method of treatment. Also, there are cases where an abnormality in a very early phase, which has not been detected by a conventional examination apparatus, can be detected by a newly-introduced examination apparatus. In this case, it can be expected to achieve the same performance as the conventional examination apparatus if an examination interval is made long.

When an optimal examination interval is calculated, it is also preferable to take into consideration such a time when a method of treatment is changed or when a new examination apparatus is introduced. A recommended examination interval can be easily and accurately calculated by using the aforementioned temporal axis search.

Data in which the examination interval is greatly different is not appropriate for sample data. With regard to this point, according to the present embodiment, data in which the examination interval is greatly different can be excluded from sample targets by setting the aforementioned second period.

The present invention has been described above based on the preferred embodiment. These embodiments are intended solely for the purpose of illustration, and it should be understood by those skilled in the art that various modifications are possible in combining those various components and various processing and those modifications also fall in the scope of the present invention.

Although a patient is not limited in the processing of calculating the aforementioned recommended examination interval in FIGS. 13 and 14, the patient may be limited to one who has been once affected by the disease and has recovered therefrom. That is, a recommended examination interval of examination for confirming presence/absence of recurrence or metastasis in the patient may be calculated.

In this case, the analysis unit 50 calculates, for every patient who has been affected by a specific disease, the days that is a difference between the examination date of examination data in which it has been diagnosed that the patient has recovered from the disease and that of the subsequent examination data in which it has been diagnosed that the disease has reoccurred or a disease related to the disease has occurred, and performs statistical processing on the days. Thereby, the recommended examination interval of a patient who has been once affected by the disease and has recovered therefrom is determined. When the examination data in which it has been diagnosed that a disease related to the disease has occurred is extracted, the name of a disease related to the disease has only to be set in the second narrowing unit 36 as a search condition.

Further, sex, age group, anamnesis, family history, and method of treatment, etc., may be added as search conditions. Furthermore, in order to increase the number of samples to be searched, it may be made to share the examination data held in the recording unit 20 and those of a similar system in another medical institution such that the search unit 30 and the analysis unit 50 can search the examination data.

What is claimed is:

1. A medical service support apparatus comprising:
a recording unit configured to hold a plurality of examination data including the examination date of a performed examination;
an operation unit configured to set a search period of examination data by an operation of a user;
a search unit configured to extract examination data matching a set condition, of the plurality of examination data held in the recording unit; and
an output unit configured to output a search result to the user by the search unit, wherein
the search unit includes:
a first narrowing indication unit configured to indicate execution of narrowing processing based on a first period set via the operation unit and on a disease name;

a first narrowing unit configured to extract, based on the indication, examination data in which the examination date is included within the first period and in which a disease of the disease name is diagnosed;

a reference data determination unit configured to classify the examination data extracted by the first narrowing unit by an examinee and to determine, for every examinee, examination data with the latest examination date as one piece of the examination data to be a reference;

a second narrowing indication unit configured to indicate, based on a second period set via the operation unit, execution of narrowing processing;

a second narrowing unit configured to extract, based on the indication and for every examinee, examination data in which the examination date is included within the second period in the past direction starting from a reference date that is the examination date of the examination data determined by the reference data determination unit and in which no abnormality has been detected; and an analysis unit, comprising a processor, configured to calculate, for every examinee, the number of days different between an examination date of the examination data in which no abnormality has been detected and an examination date of the examination data in which the disease is diagnosed and to determine a recommended examination interval for the disease by performing statistical processing on the number of the days.

2. A medical service support apparatus comprising:

a recording unit configured to hold a plurality of examination data including the examination date of a performed examination;

an operation unit configured to set a search period of examination data by an operation of a user;

a search unit configured to extract examination data matching a set condition, of the plurality of examination data held in the recording unit; and an output unit configured to output a search result to the user by the search unit, wherein the search unit includes:

a first narrowing indication unit configured to indicate execution of narrowing processing based on a first period set via the operation unit;

a first narrowing unit configured to extract, based on the indication, examination data in which the examination date is included within the first period and in which no abnormality has been detected;

a reference data determination unit configured to classify the examination data extracted by the first narrowing unit by an examinee and to determine, for every examinee, examination data with the oldest examination date as one piece of the examination data to be a reference;

a second narrowing indication unit configured to indicate, based on a second period set via the operation unit and on a disease name, execution of narrowing processing;

a second narrowing unit configured to extract, based on the indication and for every examinee, examination data in which the examination date is included within the second period in the future direction starting from a reference date that is the examination date of the examination data determined by the reference data determination unit and in which a disease of the disease name is diagnosed; and an analysis unit, comprising a processor, configured to calculate, for every examinee, the number of days different between an examination date of the examination data with the oldest examination date and an examination date of the examination data in which the disease is diagnosed and to determine a recommended examination interval for the disease by performing statistical processing on the number of the days.

* * * * *